United States Patent [19]

White et al.

[11] Patent Number: 5,466,581
[45] Date of Patent: Nov. 14, 1995

[54] METHOD FOR QUANTIFYING BPI IN BODY FLUIDS

[75] Inventors: Mark L. White, Sonoma; Stephen F. Carroll, Walnut Creek; Jeremy K.-k. Ma, San Ramon, all of Calif.

[73] Assignee: XOMA Corporation, Berkeley, Calif.

[21] Appl. No.: 175,276

[22] Filed: Dec. 29, 1993

Related U.S. Application Data

[63] Continuation-in-part of Ser. No. 125,677, Sep. 22, 1993.
[51] Int. Cl.$^6$ .................. G01N 33/53; G01N 33/543; G01N 33/68; C12Q 1/00
[52] U.S. Cl. .................. 435/7.32; 435/7.1; 435/7.9; 435/7.94; 435/7.95; 436/518
[58] Field of Search ................ 435/7.1, 7.32, 435/7.94, 7.95, 7.9; 436/518

[56] References Cited

U.S. PATENT DOCUMENTS 5,245,013  9/1993  Ulevitch et al. .................. 530/380

FOREIGN PATENT DOCUMENTS

WO94/21280  9/1994  WIPO.

OTHER PUBLICATIONS

Elsbach et al., "Separation and Purification of a Potent Bactericidal/Permeability–Increasing Protein and a Closely Associated Phospholipase A$_2$ from Rabbit Polymorphonuclear Leukocytes," *J. Biol. Chem.*, 254:11000–11009 (1979).
Gazzano–Santoro et al., "High-Affinity Binding of the Bactericidal/Permeability–Increasing Protein and a Recombinant Amino–Terminal Fragment to the Lipid A Region of Lipopolysaccharide," *Infection and Immunity*, 60(11):4754–4761 (1992).
Leturcq et al., "Generation of Monoclonal Antibodies to Human LBP and their Use in the Detection of LBP Protein in Serum," *J. Cell. Biochem.*, 16C:161 (1992).
Pereira et al., "Quantitation of a Cationic Antimicrobial Granule Protein of Human Polymorphonuclear Leukocytes by ELISA," *J. Immunol. Methods*, 117:115–120 (1989).
Pesce et al., "Cationic Antigens—Problems Associated with Measurement by ELISA," *Immunol. Methods*, 87:21–27 (1986).
Schumann, et al., "Structure and Function of Lippopolysaccharide Binding Protein," *Science*, 249:1429–1431 (Sep. 21, 1990).
Weiss, et al., "Cellular and Subcellular Localization of the Bactericidal/Permeability–Increasing Protein of Neutrophils," *Blood*, 69(2):652–659 (1987).
Weiss et al., "Human Bactericidal/Permeability–Increasing Protein and a Recombinant NH$_2$–Terminal Fragment Cause Killing of Serum–Resistant Gram–Negative Bacteria in Whole Blood and Inhibit Tumor Necrosis Factor Release Induced by the Bacteria," *J. Clin. Invest.*, 90:1122–1130 (Sep., 1992).
Weiss et al., "Purification and Characterization of a Potent Bactericidal and Membrane Active Protein from the Granules of Human Polymorphonuclear Leukocytes," *J. Biol. Chem.*, 253(8):2664–2672 (1978).
White, M. L. et al. J. Immunol. Methods 167:227–235, 1994.
Dofferhoff, A S M et al. Netherlands Journal of Medicine 39:45–62, 1991.
Spitznagel, J. K. J. Clin. Invest. 86:1381–1386, 1990.
Schindler, R. et al. Clinical Nephrology 40(6):346–351, 1993.
Taber, C. W. Taber's Cyclopedic Medical Dictionary. Philadelphia; F. A. Davis Co., 1985. p. 545.
Marra, M. N., et al. J. of Immunol. 148:532–537, 1992.
Erwin, A. L. et al. Laboratory Investigation 65(2) 138–144, 1991.
Von der Mohier et al. Abstract presented at the 13th International Symposium on Intensive Care and Emergency Medicine, Brussels, Belgium, Mar. 1993.

*Primary Examiner*—Toni R. Scheiner
*Assistant Examiner*—Eve J. Wilson
*Attorney, Agent, or Firm*—Marshall, O'Toole, Gerstein, Murray & Borun

[57] ABSTRACT

The present invention provides an immunoassay method for screening for gram negative sepsis in a subject, in which the concentration of extracellular BPI in a plasma sample from the subject is determined and compared with a standard concentration of BPI indicative of gram negative sepsis.

3 Claims, 14 Drawing Sheets

- ● Heparin
- □ 8 kDa dextran sulfate
- ■ 500 kDa dextran sulfate
- △ 1 M NaCl
- ○ Buffer control 1  2  3  4  5  6  7  8  9  10  11  12  13

— 106,000
— 80,000
— 49,500
— 32,500

1  2  3  4  5  6  7  8  9  10  11  12  13  14  15

— 106,000
— 80,000
— 49,500
— 32,500

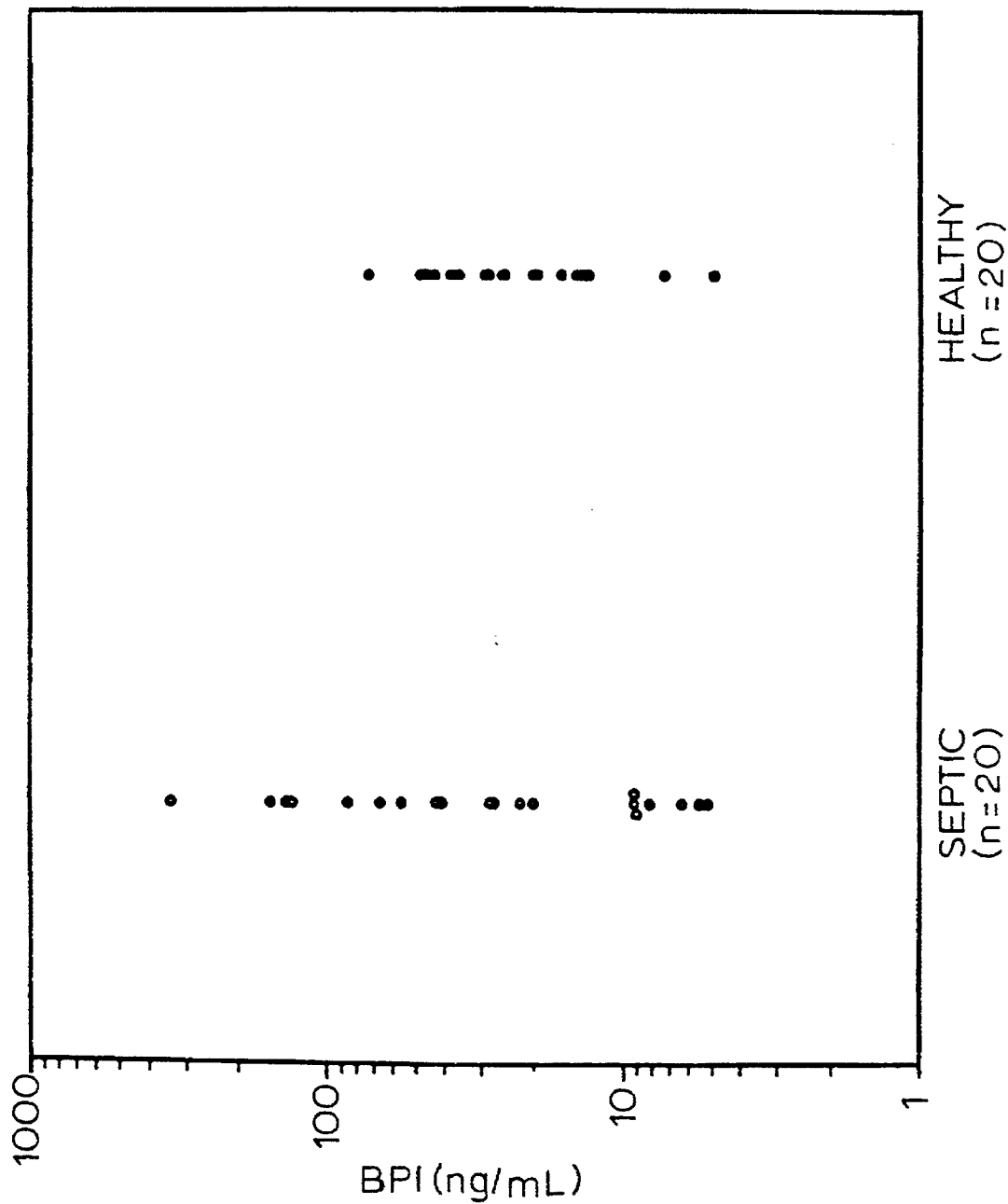

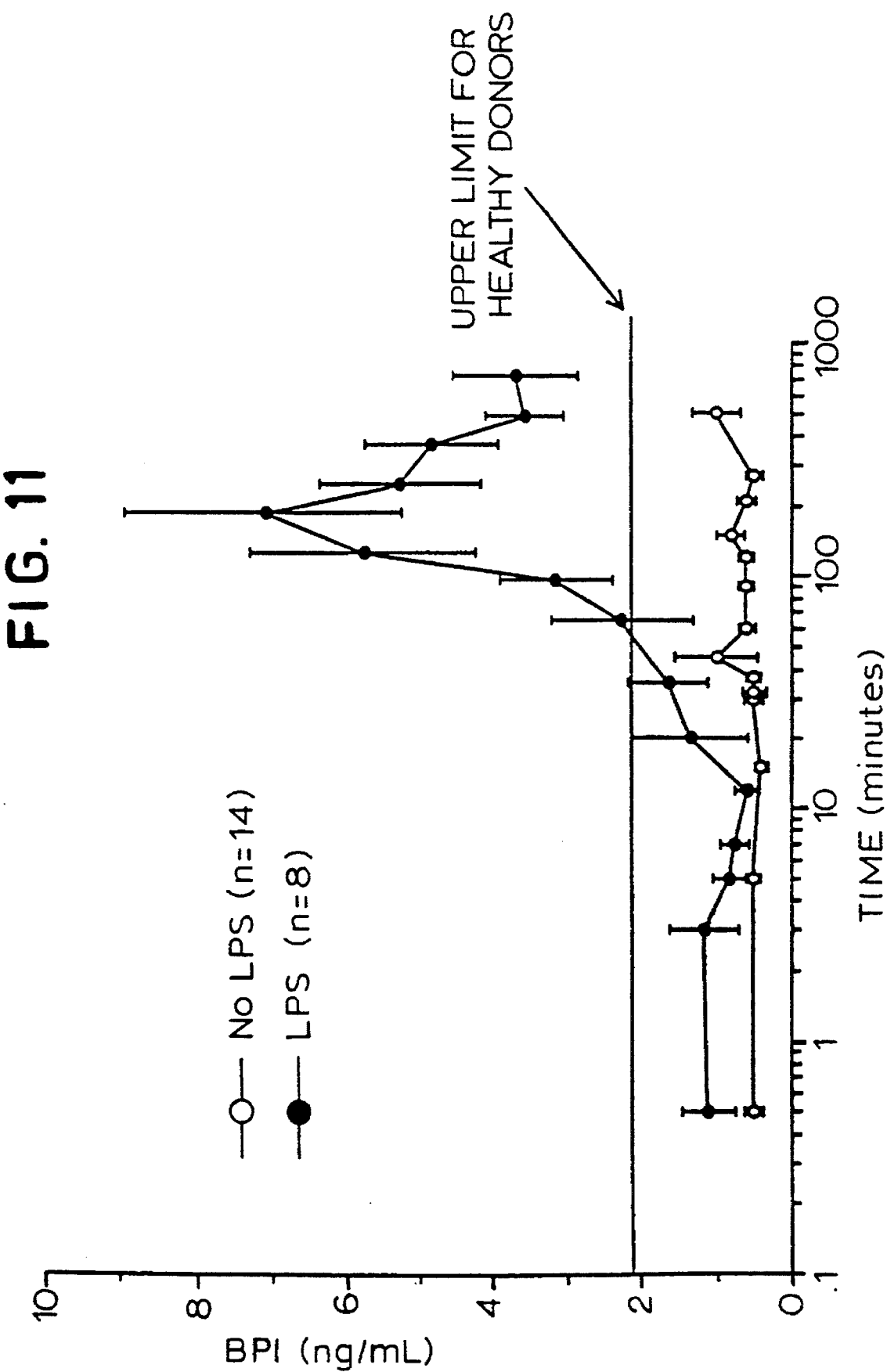

5,466,581

METHOD FOR QUANTIFYING BPI IN BODY FLUIDS

This is a continuation-in-part application of 08/125,677 filed Sep. 22, 1993.

BACKGROUND OF THE INVENTION

The present invention relates to methods for determination of the presence of Bactericidal/permeability-increasing protein in a body fluid sample including a blood sample. Bactericidal/permeability-increasing protein (BPI) is a cationic anti-microbial protein which has been purified from the azurophilic granules of human and animal neutrophils (Weiss et al., *J. Biol. Chem.*, 253:2664 (1978), Elsbach et al., *J. Biol. Chem.*, 254:11000 (1979). BPI binds to the lipopolysaccharide (LPS) component of the outer membranes of gram-negative bacteria (Gazzano-Santoro et al., *Infect. Immun.*, 60:4754 (1992)). Recently, a recombinant form of human BPI ($rBPI_{23}$) has been characterized and compared to that of native BPI. The $rBPI_{23}$ fragment consists of the amino-terminal 23 kDa portion of holo-BPI and retains the LPS binding properties, as well as the antimicrobial activity, of native BPI (Gazzano-Santoro et al., *J. Clin. Invest.*, 90:1122 (1992), Weiss, et al., *J. Clin. Invest.*, 90:1122 (1992)).

BPI levels have not previously been accurately assayed in any body fluids. Because of the potential therapeutic use of $rBPI_{23}$ and other BPI proteins and protein products, a sensitive and reproducible assay is needed to measure the presence and amount of BPI in body fluids. In particular, measurements of BPI in body fluids may be useful for diagnostic purposes. Pereira et al, *J. Immunol. Methods*, 117:115 (1989) discloses a competitive ELISA assay for the determination of BPI in crude granule extracts of human neutrophils. Pereira et al. also disclose that non-specific interactions of cationic proteins in an ELISA assay can be minimized by treatment with polyanions such as heparin or dextran sulfate. See also Pesce et al., *J. Immunol. Methods*, 87:21 (1986). However, the competitive assay of Pereira et al. is characterized by limited sensitivity. Accordingly, there remains a desire in the art for a more sensitive BPI assay capable of measuring endogenous BPI levels in mammalian body fluids. Also of interest to the present application is the disclosure of von der Mohlen et al., Abstract, 13th International Symposium on Intensive Care and Emergency Medicine, Brussels (March 1993) disclosing the results of assays for serum levels of BPI in patients with gram-negative sepsis and healthy subjects. The abstract disclosed that no BPI was detectable under the conditions of the assay in the serum of healthy subjects while circulating BPI was detected in all septic patients.

SUMMARY OF THE INVENTION

The present invention provides methods for quantifying BPI levels in body fluid samples including blood samples according to the method of conducting a BPI immunoassay on a blood sample wherein the blood sample is plasma. Plasma is the blood fluid which remains after the white and red cells are separated from fresh uncoagulated blood. Serum is the blood fluid which remains when coagulated blood is separated by centrifugation (i.e., plasma without the blood clotting factors.) As one aspect of the invention it is taught that levels of BPI present in serum are not representative of endogenous levels of BPI in circulating blood while levels of BPI in plasma are. As a further aspect of the invention methods are provided for determining the presence of gram negative sepsis in a subject comprising determining the concentration of endogenous extracellular BPI in a plasma sample obtained from that subject and comparing that concentration with a standard value indicative of gram negative sepsis. Preferred methods according to the invention determine the concentration of extracellular BPI in body fluids such as blood using a sandwich immunoassay and further utilize a cationic non-specific blocking agent selected from the group consisting of heparin and dextran sulfate in BPI immunoassays. The BPI immunoassays of the invention may also be used to determine the concentration of BPI in other body fluids including, but not limited to, serum, urine, lung lavages, vitreous fluid, crevicular fluid, cerebralspinal fluid, saliva and synovial fluid. Urine assays for BPI generally detect little or no BPI, although urine BPI levels may be elevated in subjects having urinary tract infections.

BRIEF DESCRIPTION OF THE DRAWINGS

FIG. 9a depicts a scattergram of BPI levels in the serum of healthy and septic human donors;

FIG. 11 depicts BPI levels in healthy subjects treated with LPS.

DETAILED DESCRIPTION OF THE INVENTION

Figure 1A:
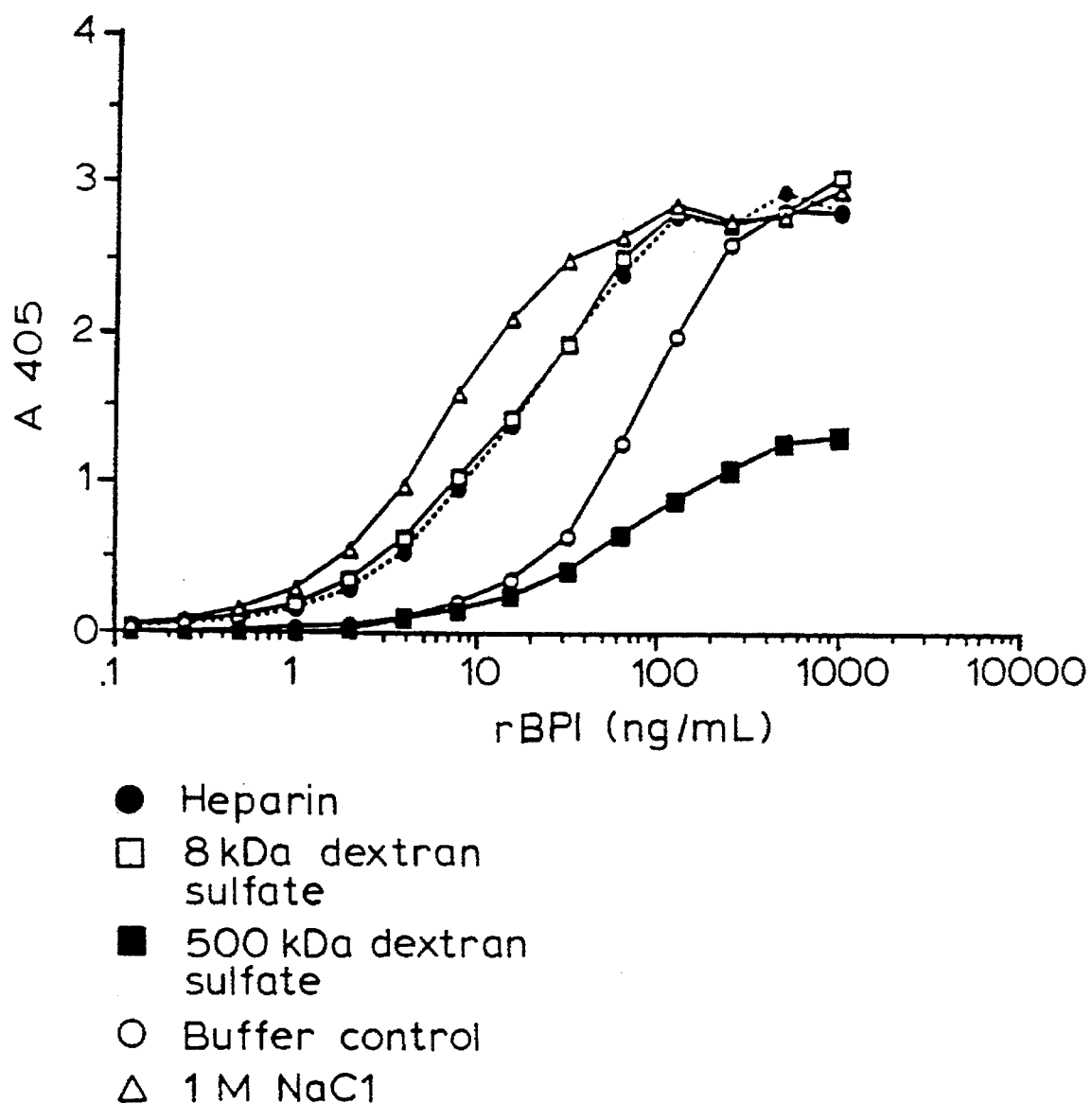
FIG. 1a depicts the effects of heparin, 8 kDa dextran sulfate, 500 Kda dextran sulfate, 1M NaCl and buffer control on the detection of RBPI in BPI sandwich ELISA assays.

The present invention relates to methods for quantifying the presence of extracellular BPI in body fluids including blood comprising conducting a BPI immunoassay on plasma obtained frown said subject. While the assay is useful for determining the presence and quantity of therapeutically administered BPI such an assay is particularly suitable for quantifying the presence of endogenous extracellular BPI in circulating blood as an indication of the presence of sepsis including grain-negative sepsis in a subject. Moreover, quantifying the presence of endogenous extracellular BPI in circulating blood is further contemplated to be useful in prognostic methods for evaluating sepsis patients.

The present invention provides a sandwich ELISA assay for human BPI which exhibits high assay sensitivity, high specificity, and excellent reproducibility. As used herein "BPI" quantitated according to assay methods includes native BPI, recombinant BPI, as well as a recombinant N-terminal fragment of BPI ($rBPI_{23}$) and other BPI proteins and protein products. Such BPI protein products may be readily quantified in the subnanogram per mL range. The immunological assays are preferably carried out by enzyme linked immunosorbant (ELISA) sandwich assays but competitive assays and immunological assays utilizing other labelling formats may also be used. Preferred assays of the invention utilize anti-BPI antibodies, including monoclonal antibodies and affinity-purified rabbit polyclonal antibodies. Rabbit polyclonal anti-BPI antibodies may be prepared according to conventional methods using BPI as an immunogen. A particularly preferred monoclonal antibody is designated Xoma 6C2 which was selected on the basis of its ability to bind BPI in solution according to conventional methodologies. According to one preferred embodiment of the invention heparin is utilized in dilution buffers. Heparin appears to improve assay performance by both reducing backgrounds and by enhancing assay signals. Similar effects are noted with low molecular weight (8 kDa) dextran sulfate. In contrast, high molecular weight dextran sulfate (500 kDa) reduces assay sensitivity, and actually reverses the beneficial effects of the low molecular weight polyanions. Initial studies revealed non-specific interactions of $rBPI_{23}$ with the microtiter plate which resulted in high background signals. Administration of heparin at 10 units/mL (approx. 55 µg/mL) reduced background signals and also improved assay sensitivity compared to buffer controls. Higher concentrations of heparin (100 units/mL) produced results similar to those observed with 10 units/mL. The inhibition caused by high molecular weight dextran sulfate may result from sterically hindering access of the antibodies to epitopes on the surface of BPI.

The addition of high salt concentrations (1M NaCl) is useful in the immunoassays of the invention for reducing background signals. The use of high salt concentrations produces greater assay sensitivities than heparin, but salt is not as effective as heparin in reducing background signals for some samples. It is believed that the enhanced sensitivity noted when samples are diluted in solutions containing heparin or high salt is due to the disruption of ionic interactions, whereas other possibly hydrophobic forces may also contribute to background signals.

The specificity of the BPI ELISA has been demonstrated in two ways. First, when immunoreactive proteins were "captured" from serum onto ELISA plates and subsequently eluted, electrophoretically separated, blotted and probed with anti-$rBPI_{23}$ antibodies, the only material detected was a doublet at ca. 60 kDa which comigrated with native BPI extracted from human neutrophils. Similarly, when identical blotted samples were probed with anti-rBPI antibodies, a significant relationship ($R^2=0.807$, $p=0.0001$) was found between the ELISA signal measured previously and the intensity of the BPI bands. Second, human LBP, which also binds to LPS and shows considerable sequence homology (44%) with BPI, generated a signal 30,000-fold to 100,000-fold lower than those generated by rBPI or $rBPI_{23}$, respectively. Even at 100 µg/ml, rLBP generated signals equivalent to less than 3 ng/ml of BPI in the ELISA. Since LBP levels in normal human serum samples have been reported (Leturcq et al, *J. Cell. Biochem.*, 16C:161 (1992)) to be between 1 and 24 µg/ml (mean 7 µg/ml), these data indicate that LBP causes minimal interference in the BPI ELISA.

As one aspect of the invention it has been found that endogenous BPI levels differ significantly depending upon whether they are assayed in human plasma or serum. Whereas normal plasma contains only low levels of BPI (<0.2 to 2.1 ng/ml), the levels in serum samples collected at the same time from the same individuals were on average 37-fold higher (4.9 to 72.1 ng/ml). Moreover, BPI levels varied depending upon the elapsed time for collection and processing. These data are important in the evaluation and interpretation of BPI levels in normal and pathologic individuals, since they suggest (i) that the plasma levels of BPI in normal individuals is quite low, and (ii) that BPI may be released from neutrophils into serum during the process of coagulation. Thus, the endogenous levels of BPI should be measured in plasma, and not in serum, thereby avoiding artifacts caused by release and/or neutrophil destruction in vitro. Similarly, the analysis of clinical samples containing recombinant forms of BPI are best performed in plasma.

Weiss and Olsson, *Blood* 69:652 (1987) have reported that neutrophils contain an average of 65 µg BPI per $10^8$ cells. Assuming that whole blood contains $5 \times 10^6$ neutrophils per ml, there would be approximately 3.2 µg/ml of BPI in 1 mL of blood. Since the concentration of BPI in serum is low (<100 ng/mL), the amount of BPI that is released during coagulation is only a small percentage (ca. 1%) of the total available material. This release of BPI may be of no physiological significance, and merely represent leakage of BPI from damaged neutrophils. Alternatively, the possibility exists that in vivo coagulation may be a general signal for the localized release of anti-microbial agents (including BPI) from neutrophils in response to injury or trauma. Under these conditions, BPI may then act as an anti-bacterial defense mechanism localized at the site of injury.

Other aspects and advantages of the present invention will be understood upon consideration of the following illustrative examples. Example 1 relates to the preparation of affinity purified rabbit anti-BPI antibodies; Example 2 relates to the biotin labeling of such antibodies; Example 3 relates to ELISA procedures utilizing such antibodies and Example 4 relates to the preparation of monoclonal anti-BPI antibodies. Example 5 relates to the effects of heparin, dextran sulfate and NaCl concentrations on sensitivity of the BPI sandwich assay; and Example 6 relates to characteristics of rBPI and $rBPI_{23}$ standard curves. Example 7 relates to the measurement of rBPI and $rBPI_{23}$ spiked into pooled human plasma; Example 8 relates to the comparative immunoreactivity of rLBP, rBPI and $rBPI_{23}$ and Example 9 relates to the effects of processing time and centrifugal force on the ELISA assay. Example 10 relates to SDS-PAGE and Western blot analysis of serum and plasma samples; and Example 11 relates to the measurement of endogenous BPI immunoreactivity in human plasma and serum. Example 12 relates to clinical correlations of BPI in sepsis patients; Example 13 relates to endogenous BPI levels in pulmonary lavage samples in normal and cystic fibrosis; Example 14 relates to endogenous BPI levels in the synovial fluid of patients suffering from rheumatoid arthritis; and Example 15 relates to the effect on endogenous BPI levels of LPS administration to healthy subjects.

Example 1

PREPARATION OF AFFINITY PURIFIED RABBIT ANTI-BPI$_{23}$ ANTIBODY

According to this example affinity purified rabbit anti-rBPI$_{23}$ antibody was prepared. Specifically, rBPI$_{23}$ (20 mg) produced according to the methods of Gazzano-Santoro et al., *Infect. Immun.* 60:4754–4761 (1992)was coupled to 10 mL of cyanogen bromide-activated Sepharose 4B (Sigma Chemical Co., St. Louis, Mo.) in 0.2M bicarbonate, pH 8.6, containing 0.5 NaCl. Approximately 97% of the rBPI$_{23}$ was coupled to the resin. Pooled antisera (150 mL) from two rabbits hyper-immunized with rBPI$_{23}$ were diluted with an equal volume of phosphate buffered saline, pH 7.2 (PBS). A portion (50 mL) of the diluted antisera was passed through the 10 mL rBPI$_{23}$-Sepharose column; the column was then washed with PBS and bound antibodies were eluted with 0.1M glycine, pH 2.5. Collected fractions were immediately neutralized with 1M phosphate buffer, pH 8.0. Peak fractions were identified by measuring absorbance at 280 nm according to the method of Harlow et al., Antibodies: A Laboratory Manual, Cold Springs Harbor Laboratory Press, N.Y. p. 312 (1988). Recovery was 45 mg of affinity purified anti-rBPI$_{23}$ antibody, or 300 micrograms of antibody per milliliter of rabbit antisera.

Example 2

PREPARATION OF BIOTIN LABELED RABBIT ANTI-BPI$_{23}$ ANTIBODY

In this example twenty milligrams of affinity purified rabbit anti-BPI$_{23}$ antibody produced according to the method of Example 1 was incubated with 2 mg of biotinamidocaproate N-hydroxysuccinimide ester (Sigma Chemical Co., St. Louis, Mo.) in 11 mL of 0.1M sodium bicarbonate pH 8.3 for two hours at room temperature. Unconjugated biotin was removed and the alkaline buffer exchanged by fractionating the reaction mixture on a PD-10 column (Pharmacia Biotech Inc., Piscataway, N.J.) equilibrated with PBS containing 0.1% sodium azide. The final yield of biotin-labeled antibody was 17.9 mg.

Example 3

ELISA PROCEDURE

Fifty microliters of affinity purified rabbit anti-BPI$_{23}$ antibody (1 µg/mL in PBS) were incubated overnight at 2°–8° C. (or alternatively, 1 hour at 37° C.) in the wells of Immulon 2 (Dynatech Laboratories Inc., Chantilly, Va.) microtiter plates. The antibody solution was removed and 200 µL of 1% non-fat milk in PBS (blocking agent) was added to all wells. After blocking the plates for 1 hour at room temperature, the wells were washed 3 times with 300 µL of wash buffer (PBS/0.05% Tween-20).

Blood from individual human donors was collected into two Vacutainer (Becton Dickinson, Rutherford, N.J.) tubes; one containing acid citrate dextrose and the second containing a clot activator and serum separator. Within 30 minutes and one hour of collection, both plasma and serum samples from an individual donor were processed simultaneously by centrifugation for 5 minutes at 1300 g. The appropriate fractions were collected and stored at − 70° C. in 0.5 mL aliquots. Pooled normal human serum and pooled citrated plasma were obtained from Sigma Chemical Co. (St. Louis, Mo.).

Standards, samples and controls were diluted in triplicate with PBS containing 1% bovine serum albumin, 0.05% Tween 20 (PBS-BSA/Tween) and 10 units/mL of sodium heparin (Sigma Chemical Co., St. Louis, Mo.) in separate 96-well plates. rBPI or rBPI$_{23}$ standard solutions were prepared as serial two-fold dilutions from 100 to 0.012 ng/mL. Each replicate and dilution of the standards, samples and controls (50 µL) was transferred to the blocked microtiter plates and incubated for 1 hour at 37° C. After the primary incubation, the wells were washed 3 times with wash buffer. Biotin-labeled rabbit anti-BPI$_{23}$ antibody was diluted ¼000 in PBS-BSA/Tween and 50 µL was added to all wells. The plates were then incubated for 1 hour at 37° C. Subsequently, all wells were washed 3 times with wash buffer. Alkaline phosphatase-labeled streptavidin (Zymed Laboratories Inc., San Francisco, Calif.) was diluted ½000 in PBS-BSA/Tween and 50 µL was added to all wells. After incubation for 15 minutes at 37° C., all wells were washed 3 times with wash buffer and 3 times with deionized water and the substrate p-nitrophenylphosphate (1 mg/mL in 10% diethanolamine buffer) was added in a volume of 50 µL to all wells. Color development was allowed to proceed for 1 hour at room temperature, after which 50 µL of 1N NaOH was added to stop the reaction. The absorbance at 405 nm was determined for all wells using a Vmax Plate Reader (Molecular Devices Corp., Menlo Park, Calif.).

The mean absorbance at 405 nm ($A_{405}$) for all samples and standards (in triplicate) were corrected for background by subtracting the mean $A_{405}$ of wells receiving only sample dilution buffer (no BPI) in the primary incubation step. A standard curve was then plotted as $A_{405}$ versus ng/mL of rBPI or rBPI$_{23}$. The linear range was selected, a linear regression analysis was performed and concentrations were determined for samples and controls by interpolation from the standard curve.

Example 4

PREPARATION OF MOUSE MONOCLONAL ANTI-BPI ANTIBODY

According to this example mouse monoclonal anti-rBPI antibody 6C2 was prepared using standard techniques according to Harlow et al., Antibodies: A Laboratory Manual. Cold Spring Harbor Laboratory Press, New York. p. 196 (1988). Specifically, a hydridoma cell line was derived from the chemical fusion of NS-1 mouse myeloma cells with splenocytes from a Balb-C mouse immunized with rBPI holoprotein. Identification of hybridoma cells secreting anti-BPI antibodies was accomplished by screening cell culture supernatants by sandwich ELISA. Hybridoma cell line 6C2 was subsequently cloned 3 times by limiting dilution. The monoclonal antibodies produced by the cell line are characterized as being of IgG1,k isotype. The hybridoma cell line has been deposited with the American Type Culture Collection 12301 Parklawn Drive, Rockville Md. 28032 and is identified as ATCC No. HB 11512.

rBPI standard curves using either the rabbit polyclonal anti-BPI antibodies or the antibodies produced by 6C2 as the capture agent showed slightly greater sensitivity achieved with the 6C2 monoclonal antibody when compared to the rabbit antibody. Immunoreactivity of rBPI$_{23}$ in the 6C2-based ELISA was approximately 1000-fold less than rBPI holoprotein. Therefore, the 6C2 monoclonal antibody readily captures rBPI or native BPI but not rBPI$_{23}$. The 6C2 BPI sandwich ELISA was also shown to exhibit minimal cross-reactivity with rLBP.

Example 5

EFFECTS OF HEPARIN, DEXTRAN SULFATE AND NaCl ON SENSITIVITY

Figure 1B:
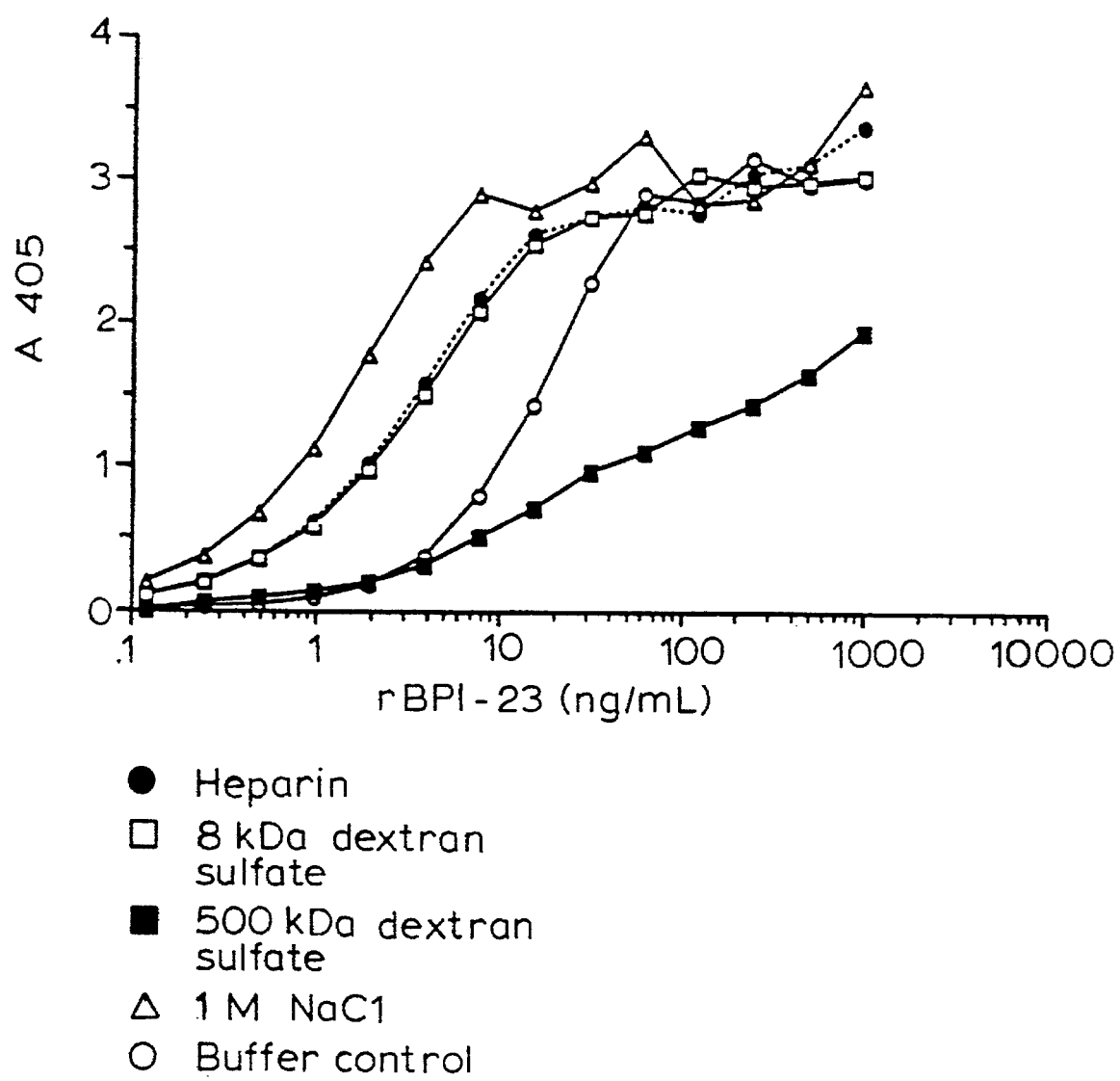
FIG. 1b depicts the effects of heparin, 8 Kda dextran sulfate, 500 kDa dextran sulfate, 1M NaCl and buffer control on the detection of $RBPI_{23}$ in BPI sandwich ELISA assays.

In this example, a comparison of the effects of heparin, dextran sulfate (Mr 8 kDa and 500 kDa) or 1M sodium chloride on BPI sandwich assay sensitivity was conducted. The results shown in FIG. 1 indicate that for both rBPI (FIG. 1a) and rBPI$_{23}$ (FIG. 1b), heparin and low molecular weight dextran sulfate (Mr 8 kDa) were equally effective on a mass basis in reducing backgrounds and increasing assay sensitivity. In contrast, high molecular weight dextran sulfate (Mr 500 kDa) reduced assay sensitivity compared to the buffer control. Although high salt caused the greatest improvement in assay sensitivity, background signals were not reduced for rBPI$_{23}$ to the same degree as with heparin. Heparin at 10 units/mL was thus utilized for all subsequent assays.

Example 6

CHARACTERISTICS OF THE STANDARD CURVES

Figure 2A:
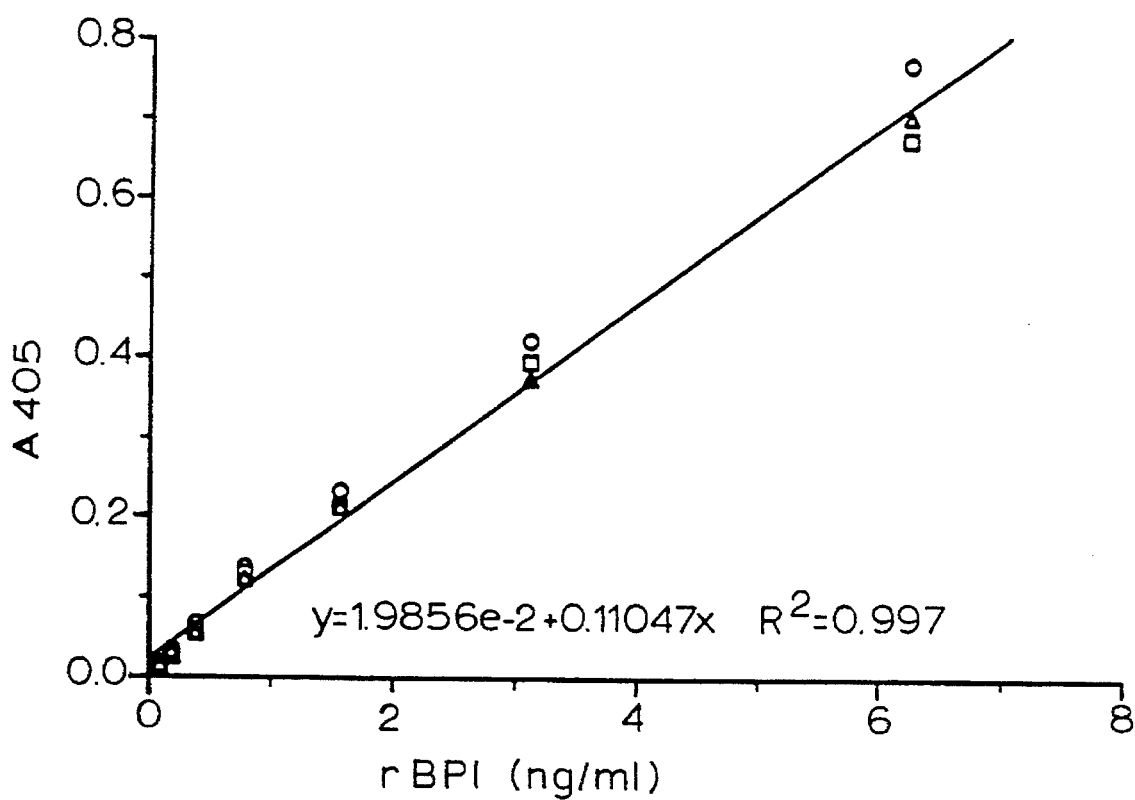
FIG. 2a depicts the reproducibility of rBPI standard curve for three separate assays in BPI sandwich ELISA assays.
Figure 2B:
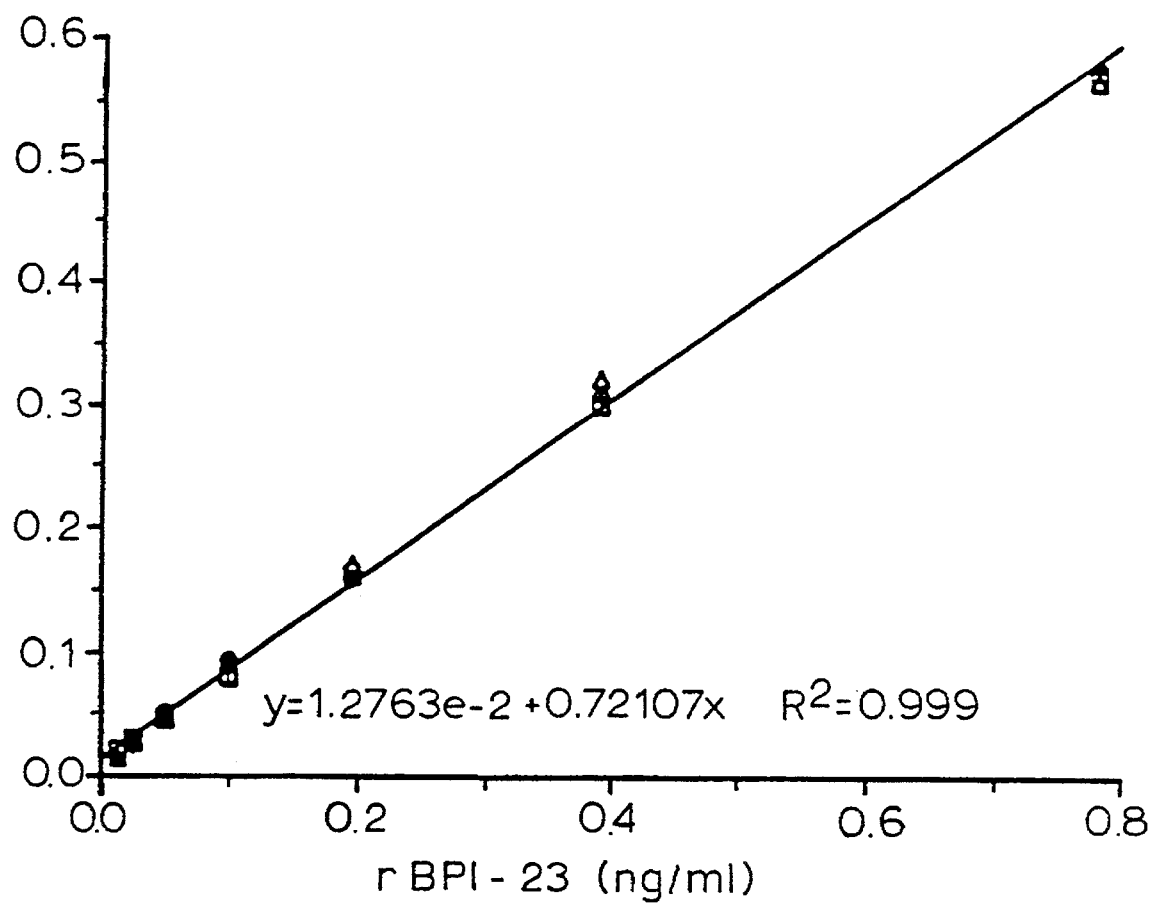
FIG. 2b depicts the reproducibility of $rBPI_{23}$ standard curve for four separate assays in BPI sandwich ELISA assays.

In this example, rBPI and rBPI$_{23}$ standard curves were found to be reproducible among several separate assays as shown in FIGS. 2a and 2b. Linear regression analysis of concentration with observed A$_{405}$ demonstrated a linear concentration response for both rBPI and rBPI$_{23}$ ($R^2$=0.997 and 0.999 respectively). The linear range was 100 to 6000 pg/mL for the rBPI standard curve and 25 to 800 pg/mL for the rBPI$_{23}$ standard curve.

Example 7

MEASUREMENT OF rBPI AND rBPI$_{23}$ SPIKED INTO POOLED HUMAN PLASMA

In this example, pooled human plasma was spiked with different concentrations of rBPI or rBPI$_{23}$ and then frozen and thawed prior to measurement in the sandwich ELISA. Recovery of spiked BPI was defined as the amount of BPI measured in spiked human plasma samples minus the concentration in the unspiked control, divided by the actual amount spiked in the sample. The fraction recovered was multiplied by 100 and the results were expressed as a percentage of the input concentration. Recovery of different concentrations of rBPI spiked into pooled human plasma samples averaged 83% and ranged from 65% at 300 ng/mL to 97% at 3 ng/mL. Recovery of rBPI$_{23}$ averaged 56% and ranged from 30% at 0.5 ng/mL to 90% at 50,000 ng/mL. Tables I and II summarize the recovery data for each BPI spiked plasma sample.

TABLE I

Recovery of rBPI$_{23}$ Spiked into Pooled Citrated Human Plasma

| Amount Spiked (ng/mL) | Amount Measured (ng/mL) | Amount Recovered (ng/mL) | Percent Recovery |
|---|---|---|---|
| 0 | 0.23 | — | — |
| 0.5 | 0.38 | 0.15 | 30% |
| 5 | 2.3 | 2.1 | 42% |
| 50 | 29 | 29 | 58% |
| 500 | 230 | 230 | 46% |
| 5,000 | 3,500 | 3,500 | 70% |
| 50,000 | 45,000 | 45,000 | 90% |
| | | Mean Recovery - | 56% |

TABLE II

Recovery of rBPI Spiked into Pooled Citrated Human Plasma

| Amount Spiked (ng/mL) | Amount Measured (ng/mL) | Amount Recovered (ng/mL) | Percent Recovery |
|---|---|---|---|
| 0 | 0.2 | — | — |
| 3 | 3.1 | 2.9 | 97% |
| 30 | 25.4 | 25.2 | 84% |
| 300 | 195 | 195 | 65% |
| 3,000 | 2,540 | 2,540 | 85% |
| | | Mean Recovery - | 83% |

Example 8

COMPARATIVE IMMUNOREACTIVITY OF rLBP, rBPI AND rBPI$_{23}$

Figure 3:
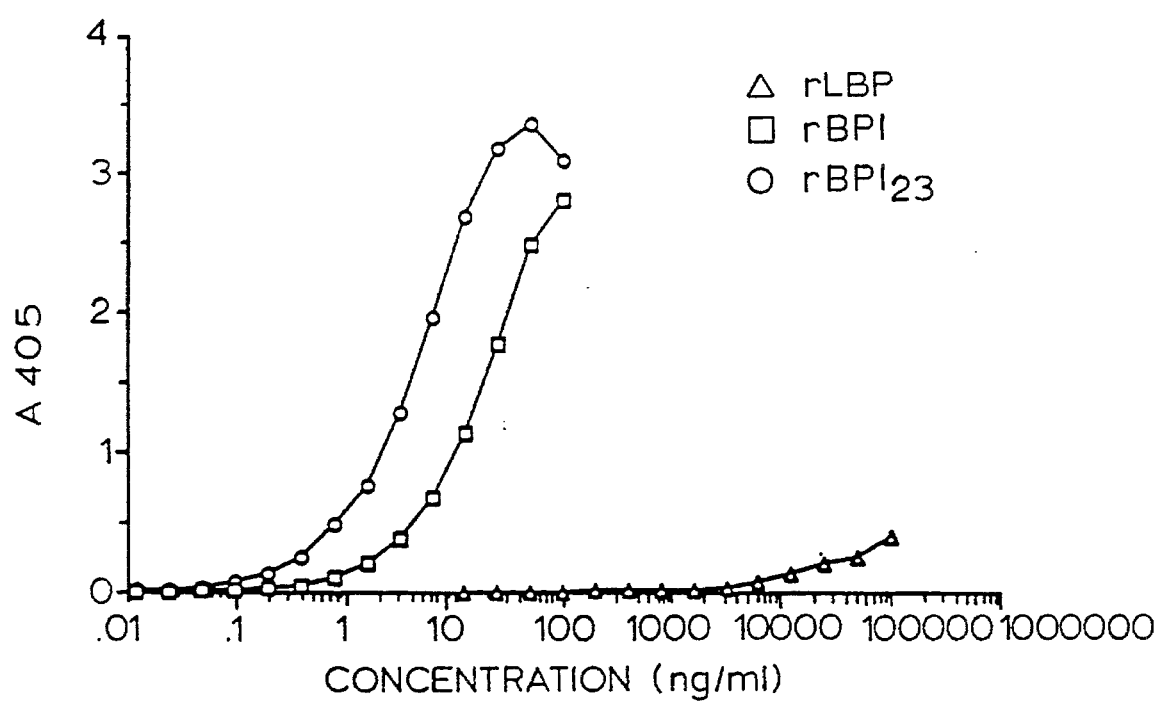
FIG. 3 depicts the dose-response curves for rLBP, RBPI and $RBPI_{23}$ in BPI sandwich ELISA assays.

In this example, the immunoreactivity of rLBP, rBPI and rBPI$_{23}$ were compared in the BPI sandwich ELISA to determine possible immunologic cross-reactivity. Despite considerable sequence homology between LBP and BPI (see Schumann et al., *Science*, 249:1429 (1990), the results illustrated in FIG. 3 show that, on a mass basis, rLBP produced a signal which was approximately 5 orders of magnitude lower than that of rBPI$_{23}$ and 4 orders of magnitude lower than that of rBPI. For example, a concentration of 100,000 ng/mL (100 µg/mL) of rLBP generated a signal which was equal to that produced by 3 ng/mL of rBPI or 0.6 ng/mL of rBPI$_{23}$. At rLBP concentrations below 3,125 ng/mL, no quantifiable signal was detected in the BPI sandwich ELISA. These results demonstrate minimal cross-reactivity of the antibody with LBP confirming the specificity of the assay for BPI.

Example 9

EFFECTS OF PROCESSING TIME AND CENTRIFUGAL FORCE

Figure 6:
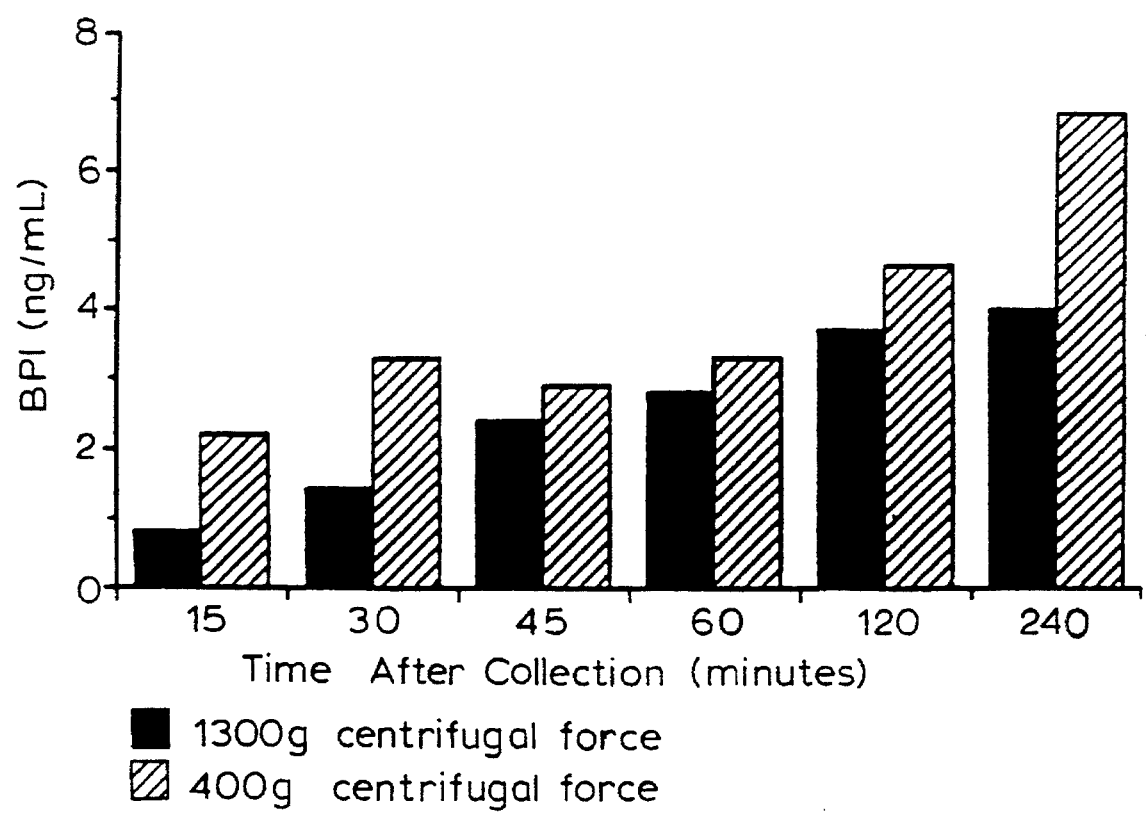
FIG. 6 depicts the effect of processing time and centrifugal force of 1300 g or 400 g on endogenous BPI levels measured by BPI sandwich ELISA in human plasma.

In this example, the effects of processing time and centrifugal force on the measurement of BPI in citrated plasma were also investigated. In general, increasing the processing time for citrated plasma increased the amount of endogenous BPI measured by the BPI sandwich ELISA when centrifugation was performed at either 400 g (cross-hatched bars) or 1300 g (solid bars) (FIG. 6). The lowest endogenous BPI levels were measured in plasma samples processed within 30 minutes of collection and at a centrifugal force of approximately 1300 g.

Example 10

SDS-PAGE AND WESTERN BLOT ANALYSIS OF SERUM AND PLASMA SAMPLES

In this example, SDS-PAGE and Western Blot analyses were conducted on serum and plasma samples. Specifically, serum and plasma samples were diluted with an equal volume of PBS-BSA/Tween containing 10 units/mL of sodium heparin. The diluted serum and plasma samples were added in a volume of 50 µL to 6 replicate wells of a microtiter plate which had been coated with affinity purified rabbit anti-rBPI$_{23}$ antibody and blocked with non-fat milk in the same manner as for the BPI sandwich ELISA described above. After a 1 hour incubation at 37° C., wells were washed 9 times with wash buffer. Captured immunoreactive material was solubilized by the sequential incubation and transfer (3 minutes per well while shaking at room temperature) of 60 μL of SDS-PAGE sample buffer (0.125M Tris-HCl, pH 6.8 containing 4% SDS, 10% glycerol, 0.004% bromphenol blue and 0.02% NaN$_3$) in the six replicate wells for each sample. Final volume of the captured and solubilized immunoreactive material for each sample was approximately 50 μL.

Fifteen microliters of each solubilized sample were run in non-reducing 10% gels under the conditions of Laemmli, *Nature,* 227:680 (1970). Proteins were transferred to nitrocellulose by standard techniques (Towbin, et al., 1979). Blotted proteins were probed for immunoreactivity with biotin-labeled rabbit anti-BPI$_{23}$ antibody (diluted 1/2000 in 0.025M Tris-HCl, pH 7.2, containing 0.2M NaCl and 0.3% Tween 20 (TBST)) or rabbit anti-rBPI antisera diluted 1/1000 in TBST. The biotin labeled rabbit anti-BPI$_{23}$ antibody was followed by alkaline phosphatase-conjugated streptavidin (Zymed Laboratories Inc., San Francisco, Calif.) diluted 1/4000 in TBST. For the unlabeled anti-rBPI antisera, an incubation with biotin labeled goat anti-rabbit IgG (Zymed Laboratories Inc., San Francisco, Calif.) diluted 1/2000 with TBST preceded the incubation with alkaline phosphatase-conjugated streptavidin. After each incubation, the blots were washed four times with TBST. Blots were immersed in a 50 μg/mL solution of the substrate 5-bromo-4-chloro-3-indolyl phosphate (Sigma Chemical Co., St. Louis, Mo.) in 0.12M veronalacetate buffer. pH 9.8 containing 0.01% (w/v) nitro blue tetrazolium and 4 mM MgCl$_2$. Color development was allowed to proceed for 1 hour at room temperature. Lanes of the Western blot were scanned with a densitometer (Shimadzu Model CS9000U, Shimadzu Corp., Kyoto, Japan) in reflectance mode and quantified by area integration.

Western blot analysis was performed on plasma and serum samples utilizing two different antibody probes to ascertain whether the ELISA immunoreactivity was due to the presence of holo-BPI, a fragment of BPI, or unrelated immunoreactive material. For these experiments, microtiter plates coated with the affinity-purified anti-BPI$_{23}$ antibody were used to capture immunoreactive material directly from plasma and serum. The affinity captured material was then eluted in sample treatment buffer, electrophoretically separated under non-reducing conditions, blotted onto nitrocellulose and then probed with anti-BPI antibodies. Referring to FIG. 7, numbers on the top of each blot identify the lane while the numbers on the right side indicate the molecular weight. Blot A. lane 1 Blank, lane 2 rLBP (100 μg/mL), lane 3 rBPI (100 ng/mL), lanes 4–12 human serum samples, lane 13 native BPI. Blot B. lanes 1–3 same as blot A, lanes 4–14 human serum samples, 15 native BPI. (Weakly visible bands were detected at 62 and 64 kDa on the nitrocellulose blot for lanes 7, 10 and 12 on blot A and lanes 4, 5, 6, and 14 on blot B, but the bands did not reproduce well in the figure. Bands were also detected at 69.5 and 114.4 kDa on the nitrocellulose blot for lane 2 on both blots A and B, but reproduced poorly in the figure.) When the blots were probed with affinity purified anti-BPI$_{23}$ antibody, the ELISA immunoreactivity appeared to correlate with the presence of two bands with apparent molecular weights of 62,000 and 64,000 Da. Native BPI extracted from human neutrophils also migrated as two bands at 62,000 and 64,000 Da. A faint band at 50 kDa was detected in both the BPI extracted from neutrophils and in the BPI derived from a few human serum samples (this is not visible in FIG. 7). This band may represent a non-glycosylated form of BPI (Mr 50,659) and was less than 7% of the total BPI detected. rBPI migrated as single band at 64,000 Da. No other immunoreactive bands were visible on the Western blots for these plasma or serum samples. rBPI$_{23}$ spiked into human plasma was also detected by these methods and was readily distinguishable from rBPI and native BPI (data not shown). When rLBP was added to anti-BPI$_{23}$ coated wells at 100,000 ng/mL and processed as described above, two weakly immunoreactive bands were discernible with an apparent molecular weight of 69,500 and 114,400 Da (this is not visible in FIG. 7). The combined intensities (measured as integrated peak area) of the rLBP bands were approximately 5,000 fold lower than the rBPI peak area, on a mass basis.

Figure 8:
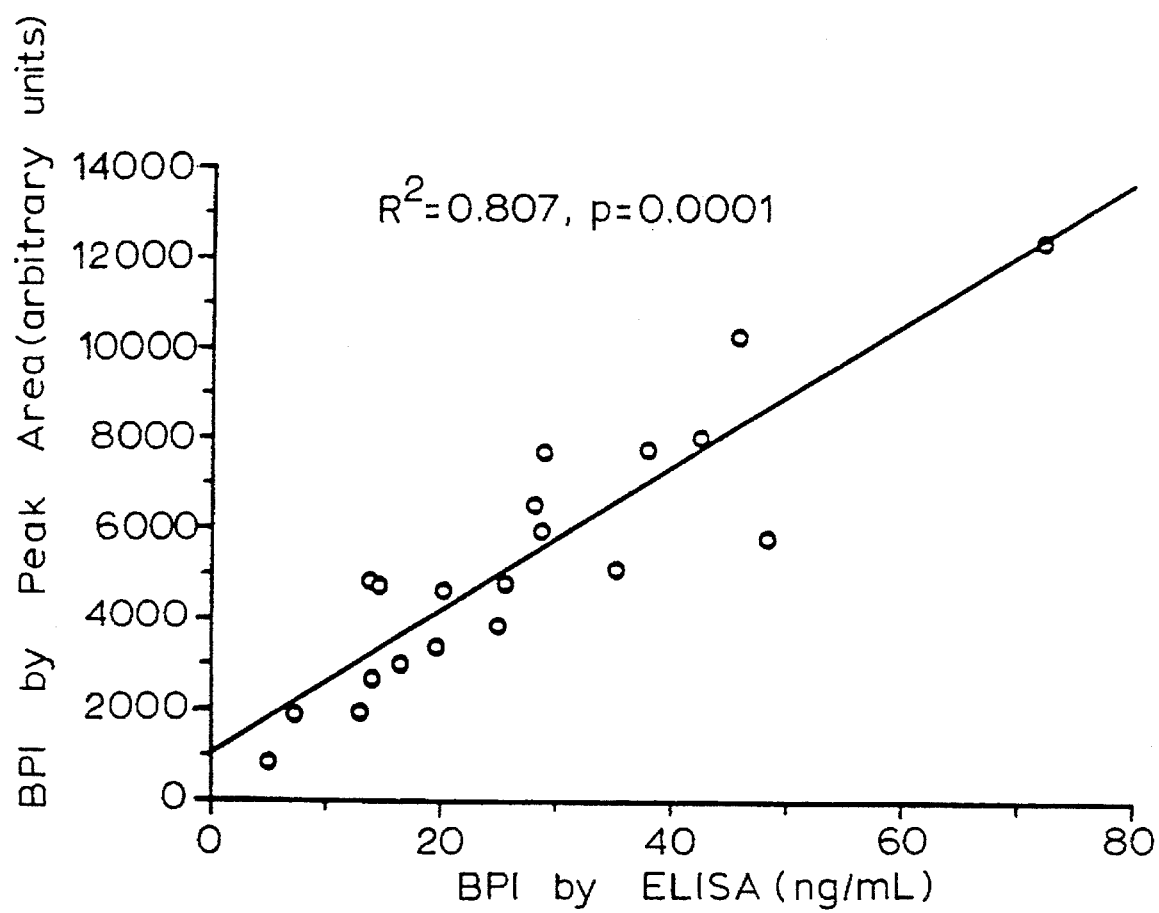
FIG. 8 depicts the relationship of Western blot integrated peak area for two BPI bands (Mr 62 and 64 kDa) with BPI sandwich ELISA immunoreactivity for 20 human serum samples.

When these same serum samples were probed with the anti-rBPI antisera, the ELISA immunoreactivity again correlated with the presence of the protein doublet at 62,000/64,000 Da and a significant relationship ($R^2=0.807$, $p=0.0001$) was observed between the ELISA signal and the Western blot integrated peak areas for the two BPI bands (FIG. 8). rLBP spiked at 100 μg/mL was not detectable when probed with the anti-rBPI antisera. These data suggest that the endogenous immunoreactivity of serum and plasma detected by ELISA is due to holo-BPI and not due to fragments of BPI or other cross-reactive material.

Example 11

MEASUREMENT OF ENDOGENOUS BPI IMMUNOREACTIVITY IN HUMAN PLASMA AND SERUM

Figure 4:
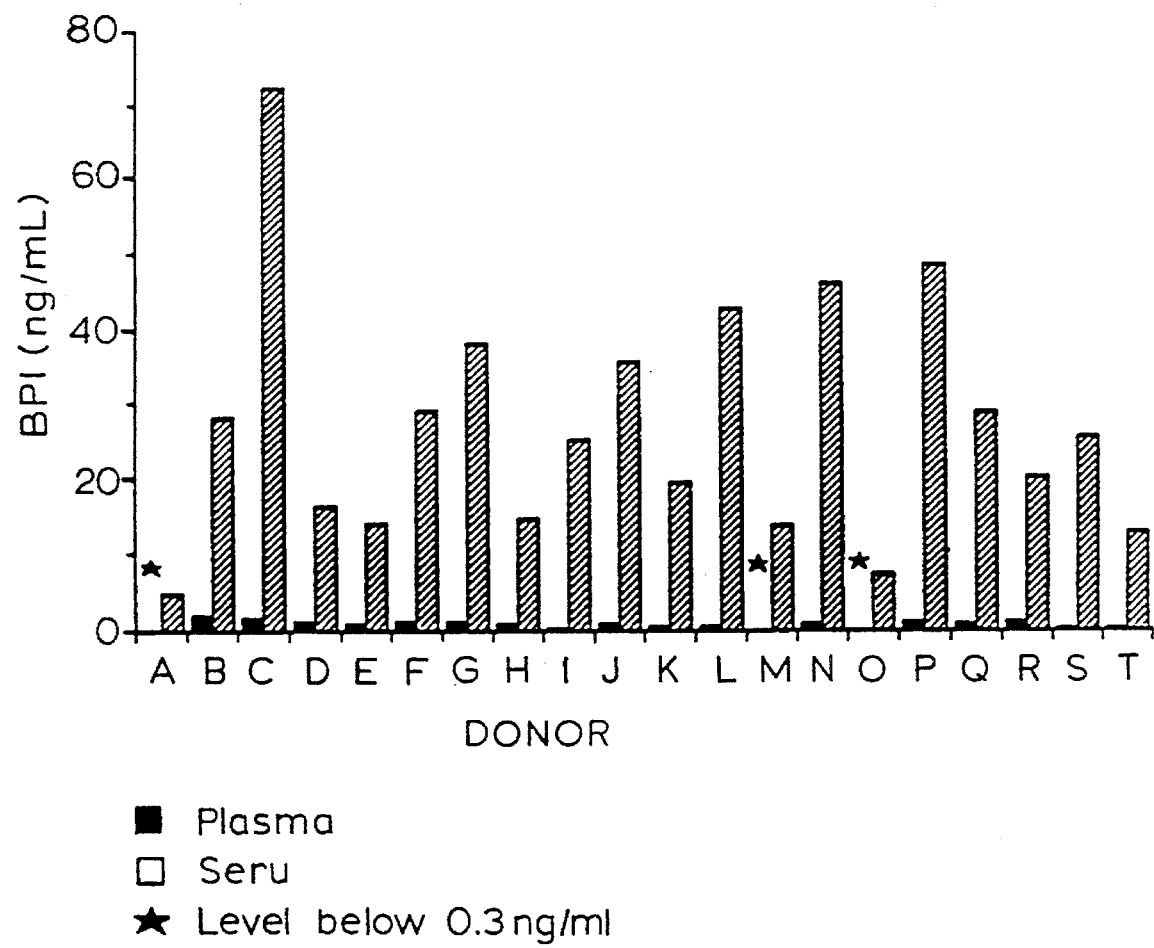
FIG. 4 depicts endogenous BPI levels in matched plasma and serum samples for 20 different healthy human donors.

In this example, endogenous BPI immunoreactivity in human plasma and serum was determined. Plasma and serum samples were collected from 20 different healthy human donors. Utilizing the BPI sandwich ELISA and rBPI as the standard, BPI levels (ng/mL) were determined for each of these samples. For all individuals tested, the results shown in FIG. 4 show that BPI levels were consistently higher in the serum samples (cross-hatched bars) compared to the matched plasma samples (solid bars). The mean BPI concentration was 0.8 ng/mL in plasma and 27.1 ng/mL in serum. The concentration range of BPI was <0.2 to 2.1 ng/mL in plasma and 4.9 to 72.1 ng/mL in serum.

Figure 5:
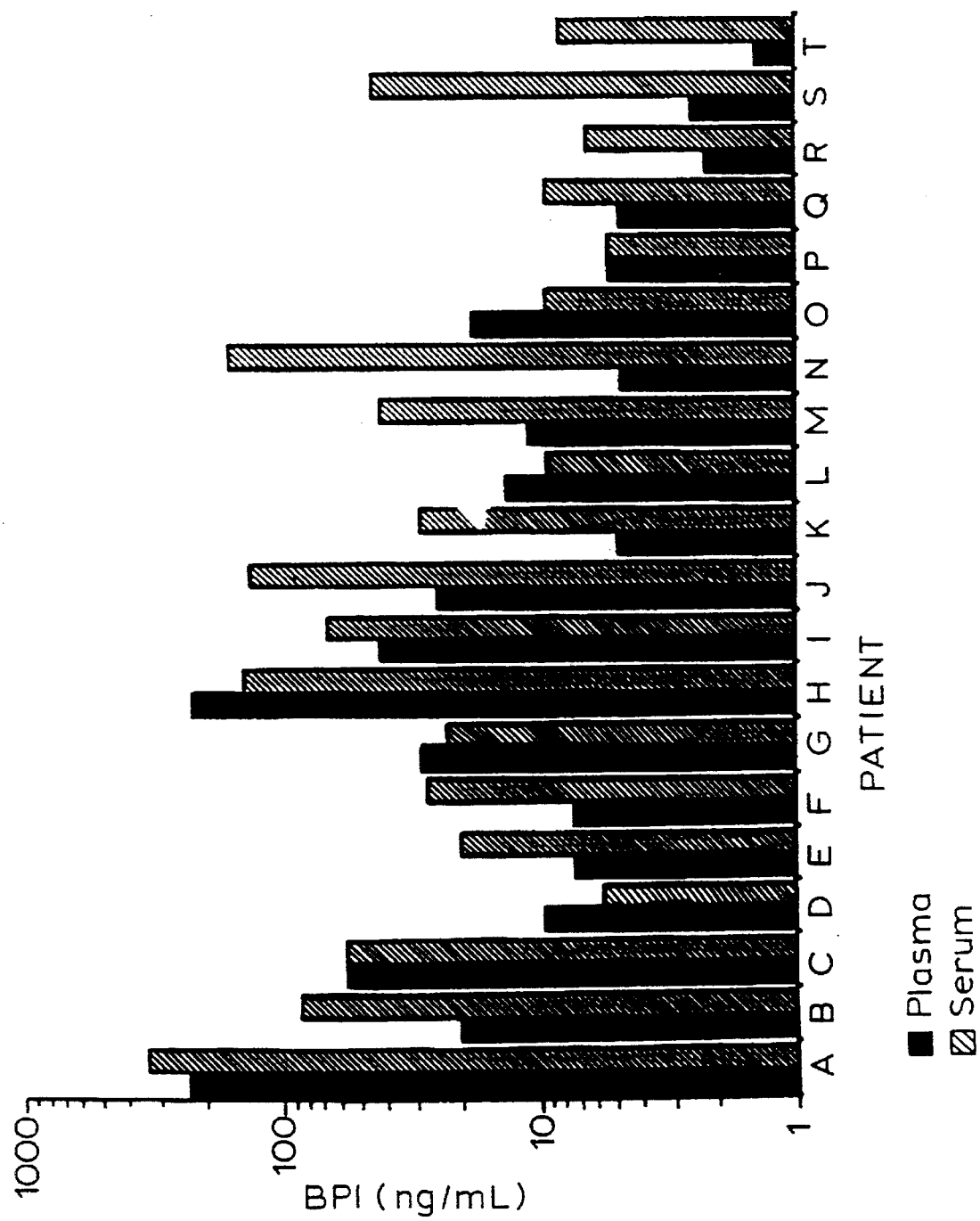
FIG. 5 depicts endogenous BPI levels in matched plasma and serum samples for 20 different human donors suffering from sepsis.
Figure 9B:
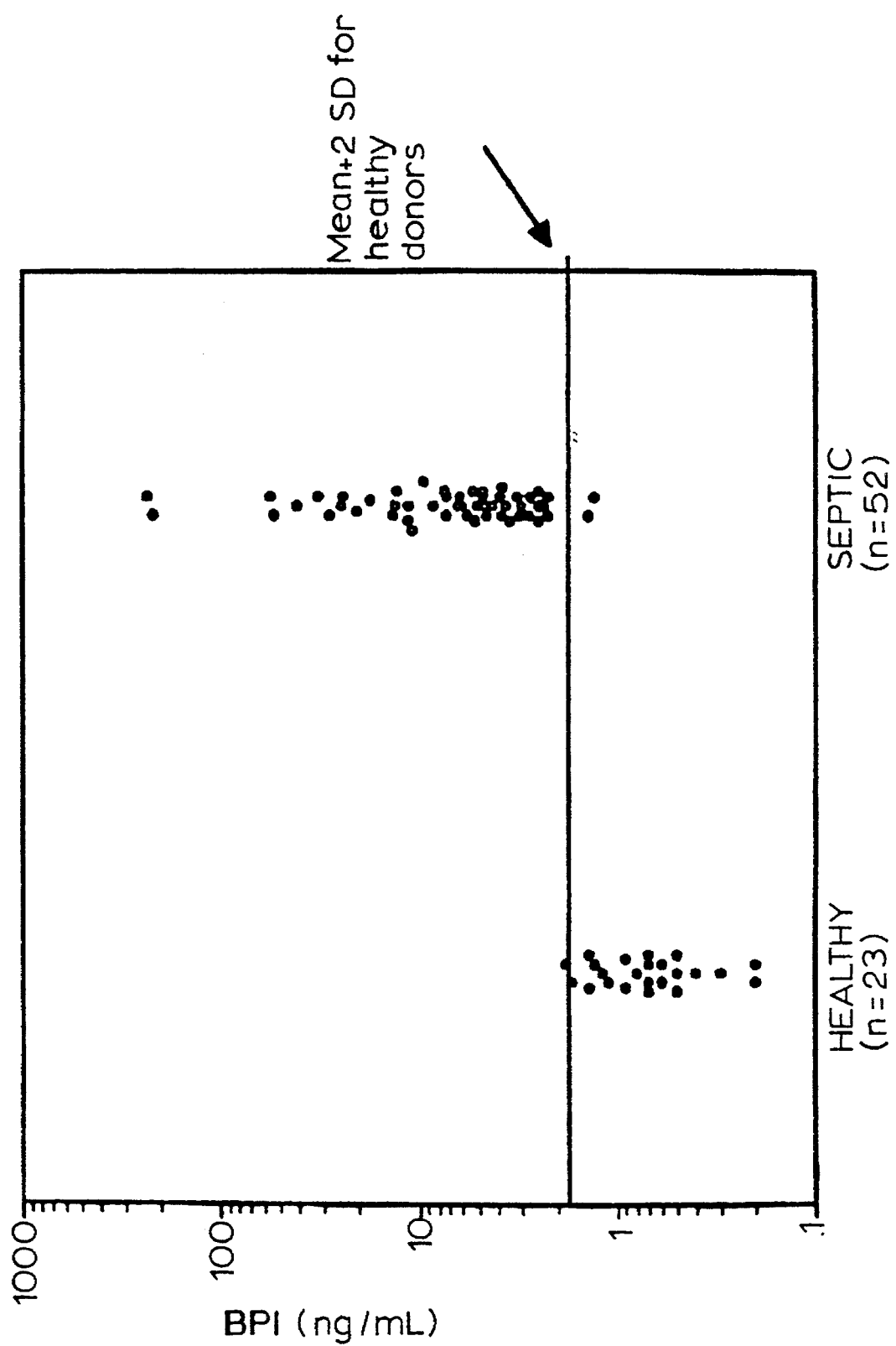
FIG. 9b depicts a scattergram of BPI levels in the plasma of healthy and septic human donors.

The experiment was then repeated for plasma and serum samples collected frown 20 sepsis patients. The results shown in FIG. 5 show that the plasma and serum levels are not identical for the same patient. Moreover, the BPI levels are different from those of the healthy patients where the plasma BPI levels were always low. Statistical analysis of BPI levels in the serum of normal and septic patients shows that there is no statistically significant difference between the two ($p=0.10$). A scattergram showing BPI levels in the serum of healthy and septic individuals is shown in FIG. 9a. In contrast, the differences in BPI levels in the plasma of normal and septic patients is highly statistically significant ($p=0.0014$) as shown by the scattergram of FIG. 9b.

Example 12

CLINICAL CORRELATIONS OF ENDOGENOUS BPI IMMUNOREACTIVITY IN HUMAN PLASMA IN SEPSIS PATIENTS

In this example, endogenous BPI immunoreactivity in human plasma samples collected from 66 patients with sepsis of suspected Gram negative etiology was quantified using the BPI sandwich assay and the levels of BPI were correlated with a variety of clinical parameters and measurements taken from the same samples. In addition, correlations were made between BPI levels and survival over a 30 day period. To simplify the survival analysis, the median level of BPI for these samples was calculated to be 4.8 ng/mL, and this level was used to stratify the patients into those with high levels of BPI (>4.8 ng/mL) and those with low levels of BPI (<4.8 ng/mL). When the data from 59 patients was stratified in this manner there was an apparent relationship between endogenous levels of BPI and 14-day survival. Specifically, subjects with BPI levels below the median had higher 14-day survival levels suggesting that lower BPI levels correlate with higher survival although the correlation was not statistically significant. No difference between the two groups was observed with respect to 30 day survival rates.

The results disclosed an apparent inverse correlation between pretreatment BPI levels and both age and APACHE II (Acute Physiology Age Chronic Health Evaluation) scores. APACHE II scores are prognostic of long term survival with lower APACHE II scores indicating a better chance for survival. Accordingly, higher initial endogenous BPI levels correlated with a better chance for long term survival according to the APACHE II score despite the negative correlation with 14 day survival. The results indicated no relationships between initial endogenous BPI levels and (i) hours since diagnosis, (ii) white blood cell counts, (iii) absolute neutrophil counts, (iv) platelet counts, (v) number of morbidities, (vi) number of major/minor morbidities, (vii) gender, (viii) ethnicity, (ix) infection type, or (x) type of morbidity.

Example 13

ENDOGENOUS BPI LEVELS IN PULMONARY LAVAGE SAMPLES IN NORMAL AND CYSTIC FIBROSIS PATIENTS

In this example, endogenous BPI immunoreactivity in pulmonary lavage samples obtained from normal individuals and cystic fibrosis patients was compared. In general, the BPI concentrations from pulmonary lavage samples obtained from the normal human subjects were less than 0.05 ng/mL with pulmonary lavage samples from cystic fibrosis patients exhibiting elevated concentrations of BPI in the range from 10 ng/mL to 100 ng/mL and higher.

Example 14

ENDOGENOUS BPI LEVELS IN SYNOVIAL FLUID SAMPLES FROM RHEUMATOID ARTHRITIS PATIENTS

Figure 10:
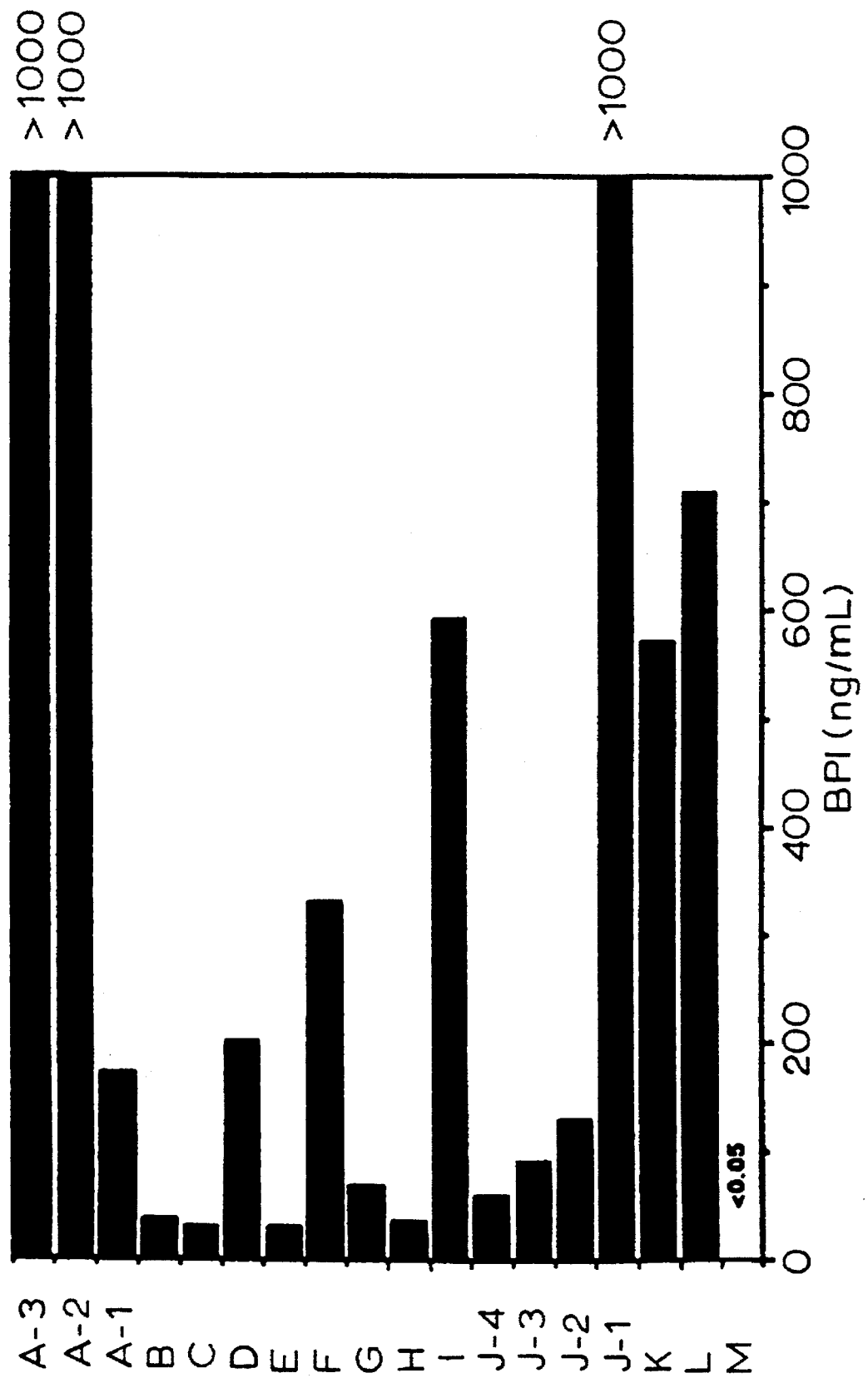
FIG. 10 depicts BPI levels in synovial fluids obtained from rheumatoid arthritis patients.

In this example, endogenous BPI immunoreactivity in the synovial fluids of rheumatoid arthritis patients was determined utilizing the BPI sandwich assay. Synovial fluid samples were obtained from arthritic joints of 13 patients suffering from rheumatoid arthritis with some samples taken from the same patient at different dates. Due to the high viscosity of synovial fluids, these samples were treated with hyaluronidase at a final concentration of 100 units/mL for 15 minutes at 37° C. and then centrifuged for 10 minutes at 10,000 g. The results of analysis of those samples presented in FIG. 10 show elevated concentrations of BPI in excess of 25 ng/mL for all but one of the samples. The concentrations of BPI in synovial fluid are substantially in excess of those in the plasma of healthy subjects and may be indicative of the presence or severity of an active arthritic condition.

Example 15

THE EFFECT OF LPS ADMINISTRATION ON ENDOGENOUS BPI LEVELS IN HEALTHY SUBJECTS

In this example, the effect of LPS administration on endogenous BPI immunoreactivity in healthy human subjects was determined. Specifically, healthy subjects were monitored utilizing the BPI sandwich assay for changes in BPI plasma levels at various time points after intravenous administration of 4 ng/kg LPS (8 subjects) or no LPS (14 subjects). The results illustrated in FIG. 11 show the change in mean plasma BPI concentration with time. For those subjects treated with LPS BPI levels began to rise one hour after LPS administration. Peak BPI plasma levels were observed in most subjects between 2 to 4 hours after the LPS administration. The average increase from baseline to peak BPI level was approximately 8-fold. Over this time period the mean BPI levels in control subjects remained within the normal range (< 2.1 ng/mL).

It is contemplated that additional analysis will illustrate the correlation of BPI plasma levels with symptoms of bacterial infections, endotoxemia and sepsis including conditions associated with sepsis including DIC and ARDS.

Numerous modifications and variations in the practice of the invention are expected to occur to those skilled in the an upon consideration of the foregoing description of the presently preferred embodiments thereof. Consequently, the only limitations which should be placed upon the scope of the present invention are those which appear in the appended claims.

What is claimed is:

1. An immunoassay method for screening for gram-negative sepsis in a subject comprising determining the concentration of extracellular BPI in a plasma sample obtained from said subject, wherein said immunoassay comprises the steps of obtaining said plasma sample from said subject, contacting said plasma sample with antibodies which specifically bind to BPI, detecting said BPI bound to said antibodies to determine the concentration of said BPI in said sample, and comparing said concentration with a standard concentration of BPI indicative of gram-negative sepsis.

2. The method of claim 1 wherein said immunoassay is a sandwich immunoassay.

3. The method of claim 1 wherein the immunoassay is conducted in the presence of a cationic non-specific blocking agent selected from the group consisting of heparin and dextran sulfate.

* * * * *

UNITED STATES PATENT AND TRADEMARK OFFICE
CERTIFICATE OF CORRECTION

PATENT NO. : 5,466,581
DATED : November 14, 1995
INVENTOR(S) : WHITE ET AL.

It is certified that error appears in the above-indentified patent and that said Letters Patent is hereby corrected as shown below:

Column 2, line 66, "obtained frown" should be --obtained from--.

Column 12, line 34, "in the an" should be --in the art--.

Signed and Sealed this

Tenth Day of December, 1996

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,466,581
DATED : November 14, 1995
INVENTORS : WHITE ET AL.

Figure 7A:
FIG. 7 depicts Western Blot immunoreactivity of material captured by affinity-purified anti-$BPI_{23}$ antibody coated microtiter wells.
Figure 7B:
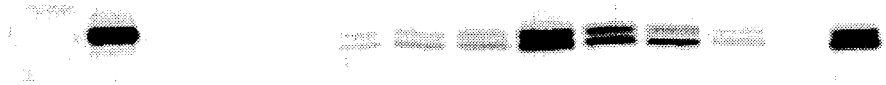

It is certified that error appears in the above-identified patent and that said Letters Patent is hereby corrected as shown below:

Column 2, line 43, "FIG. 7 depicts" should be --Figs. 7A and 7B depict--.

Column 9, line 46, "to FIG. 7," should be --to Fig. 7A and Fig. 7B--.

Column 9, line 46, "each blot identify" should be --each blot (Fig. 7A depicts Blot A and Fig. 7B depicts Blot B) identify--.

Column 9, line 65, "in FIG. 7)." should be --in Fig. 7A and Fig. 7B).--

Column 10, line 9, "in FIG. 7)." should be --in Fig. 7A and Fig. 7B).--

Signed and Sealed this

First Day of April, 1997

Attest:

BRUCE LEHMAN

Attesting Officer

Commissioner of Patents and Trademarks